(12) United States Patent
Liou et al.

(10) Patent No.: US 7,741,495 B2
(45) Date of Patent: Jun. 22, 2010

(54) INDOLINE-SULFONAMIDES COMPOUNDS

(75) Inventors: Jing-Ping Liou, Taipei (TW);
Jang-Yang Chang, Taipei (TW);
Hsing-Pang Hsieh, Taipei (TW)

(73) Assignees: Taipei Medical University (TW);
National Health Research Institutes (TW)

( * ) Notice: Subject to any disclaimer, the term of this patent is extended or adjusted under 35 U.S.C. 154(b) by 204 days.

(21) Appl. No.: 11/798,079

(22) Filed: May 10, 2007

(65) Prior Publication Data

US 2008/0058386 A1   Mar. 6, 2008

(30) Foreign Application Priority Data

Aug. 31, 2006   (TW) .................................. 95132140

(51) Int. Cl.
*C07D 209/44*   (2006.01)
*A61K 31/41*   (2006.01)

(52) U.S. Cl. ....................... 548/469; 514/359
(58) Field of Classification Search ....................... None
See application file for complete search history.

(56) References Cited

OTHER PUBLICATIONS

Chang et. al. Journal of Medicinal Chemistry (2006) 49:6656-6659.*

Dorwald F. A. (Side reactions in organic synthesis, 2005, Wiley, VCH, Weinheim, p. IX of Preface).*

* cited by examiner

*Primary Examiner*—Frederick Krass
*Assistant Examiner*—Marcos Sznaidman
(74) *Attorney, Agent, or Firm*—Bacon & Thomas, PLLC

(57) ABSTRACT

A series of indoline-sulfonamide compounds is disclosed. The formula of indoline-sulfonamide compounds is shown as formula (I). In formula (I), $R^1$ is H or halogen; $R^2$ is Ar, Ar—C(O)—, Ar—CH$_2$—, Ar—SO$_2$—, Ar—O—C(O),

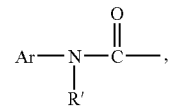

or R"—C(O)—, and Ar is a substituted or unsubstituted C5-C20 aryl, cyclyl, heterocyclyl, or heteroaryl, R' and R" independently is C1-C10 alkyl, or C1-C10 alkoxyl; and $R^3$ is C5-C15 aryl or C1-C10 alkyl. The indoline-sulfonamide compounds disclosed in the present invention are characterized in inhibiting tubulin polymerization, and treating cancers and other tubulin polymerization-related disorders with a suitable pharmaceutical acceptable carrier.

25 Claims, No Drawings

INDOLINE-SULFONAMIDES COMPOUNDS

BACKGROUND OF THE INVENTION

1. Field of the Invention

The present invention relates to an indoline-sulfonamide compound and, more particularly, to an indoline-sulfonamide compound for inhibiting tubulin polymerization.

2. Description of Related Art

The microtubule system of eukaryotic cells is an important target for the development of anticancer agents. For a more concrete description, the tubulin polymerization/depolymerization is a popular target for the development of new chemotherapy agents. A number of clinically used agents (such as paclitaxel, epothilone A, vinblastine, combretastatin A-4 (CA-4), dolastatin 10, and colchicines), taking tubulin polymerization/depolymerization as the target, all exhibit their anticancer properties by disrupting cellular microtubule structure and function resulting in mitotic arrest, as well as inhibiting the growth of epithelium of newly formed vasculature to shut down the blood supply to tumors (please refer to Jordan et. al., (1998) Med. Res. Rev. 18: 259-296).

Therefore, according to the microtubule system (such as tubulin polymerization/depolymerization) as the target for developing compounds, the new therapy used for the treatment or the prevention of cancers or cancer related symptoms, or the treatment of angiogenesis related disease, such as cardiovascular disease (e.g. atherosclerosis), chronic inflammation (e.g. rheumatoid arthritis or Crohn's disease), diabetes (e.g. diabetic retinopathy), psoriasis, and retinal neovascularization or corneal neovascularization can be developed (please refer to Griggs rt. al., (2002) Am. J. Pathol. 160(3): 1097-1103).

A variety of synthetic small molecules have been reported as inhibitors of tubulin polymerization, which compete the colchicine-binding site to tubulin. Structurally, they involve various heteroaromatic cores, for instance including the indole, benzothiophene, benzofuran, imidazole, thiazole, and oxadiazoline moieties. The indole system has a majority, for example 2-aroylindoles, 3-aroylindoles, 3-aroyl-2-phenylindoles, 3-arylthioindoles-2-carboxylate, and indolyl-3-glyoxamides that show strong antiproliferative and antitubulin activity.

The sulfonamide-containing compounds, such as N-pyridinyl sulfonamide ABT-751 (formerly E-7010) and styrylpyridine N-oxide sulfonamide HMN-21416, demonstrated effective inhibitor of tubulin polymerization and a potent antimitotic agent, respectively. ABT-751 and HMN-214 are now undergoing human clinical trials against various tumor types. So far, there have been no reports on the inhibition of tubulin polymerization by Indoline-sulfonamides.

SUMMARY OF THE INVENTION

The present invention relates to a novel 7-aroylaminoindoline-1-sulfonamide series as highly potent inhibitors of tubulin polymerization.

The present invention provides an indoline-sulfonamide compound as the following formula (I):

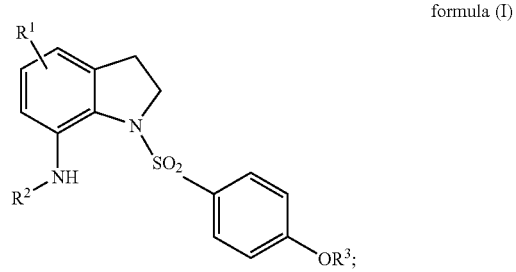

formula (I)

wherein $R^1$ is H, or halogen;
$R^2$ is Ar, Ar—C(O)—, Ar—CH$_2$—, Ar—SO$_2$—, Ar—O—C(O),

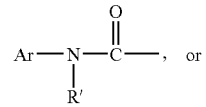

, or $R''$—C(O)—, and Ar is substituted or unsubstituted C5-C20 aryl, cyclyl, heterocyclyl, or heteroaryl, R' and R'' independently is C1-C10 alkyl, or C1-C10 alkoxyl; and
$R^3$ is C5-C15 aryl or C1-C10 alkyl.

The hetero-atom of the heterocyclyl or heteroaryl is not limited. Preferably, the hetero-atom is N, O, or S. Preferably, the heteroaryl is

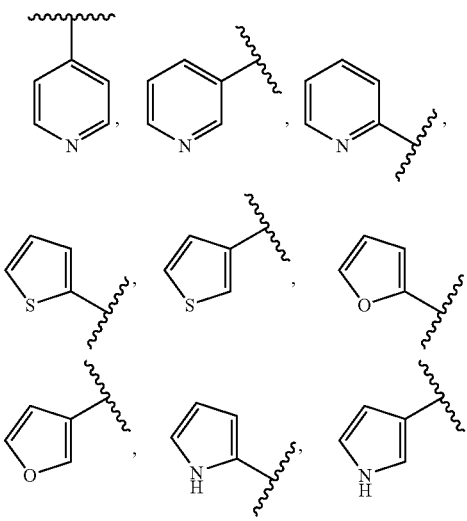

Preferably, $R^1$ is H, or halogen (e.g. F, Cl, Br, I). More preferably, $R^1$ is H or Br.

The structure of Ar is not limited. Preferably, Ar is unsubstituted phenyl, substituted or unsubstituted C5-C8 aryl or heteroaryl, or aryl with a substituent. Preferably, the substituent is halogen, nitro, cyano, alkoxyl, oxyl, or acetoxyl (CH$_3$CO$_2^-$). Preferably, the halogen is F, Cl, or Br.

Preferably, $R^2$ is benzoyl, fluorobenzoyl, nitrobenzoyl, cyanobenzoyl, methoxybenzoyl, acetylbenzoyl, isonicotinoyl, N-oxide-isonicotinoyl, furoyl, thienoyl, benzenesulfonyl, nitrobenzenesulfonyl, fluorobenzenesulfonyl, (CO)OC$_6$H$_5$, (CO)N(CH$_3$)C$_6$H$_5$, benzyl, acetyl, or pivaloyl.

Preferably, $R^3$ is C1-C10 alkyl. More preferably, $R^3$ is methyl.

The preferred examples of the indoline-sulfonamide compounds of the present invention are:

1-(4-Methoxy-benzenesulfonyl)-2,3-dihydro-1H-indol-7-ylamine (compound 19),
N-[1-(4-Methoxy-benzenesulfonyl)-2,3-dihydro-1H-indol-7-yl]-benzamide (compound 20),
4-Fluoro-N-[1-(4-methoxy-benzenesulfonyl)-2,3-dihydro-1H-indol-7-yl]-benzamide (compound 21),
N-[1-(4-Methoxy-benzenesulfonyl)-2,3-dihydro-1H-indol-7-yl]-4-nitro-benzamide (compound 22),
4-Cyano-N-[1-(4-methoxy-benzenesulfonyl)-2,3-dihydro-1H-indol-7-yl]-benzamide (compound 23),
4-Methoxy-N-[1-(4-methoxy-benzenesulfonyl)-2,3-dihydro-1H-indol-7-yl]-benzamide (compound 24),
N-[1-(4-Methoxy-benzenesulfonyl)-2,3-dihydro-1H-indol-7-yl]-terephthalamic acid methyl ester (compound 25),
N-[1-(4-Methoxy-benzenesulfonyl)-2,3-dihydro-1H-indol-7-yl]-isonicotinamide (compound 26),
Furan-2-carboxylic acid [1-(4-methoxy-benzenesulfonyl)-2,3-dihydro-1H-indol-7-yl]-amide (compound 27),
Thiophene-2-carboxylic acid [1-(4-methoxy-benzenesulfonyl)-2,3-dihydro-1H-indol-7-yl]-amide (compound 28),
N-[1-(4-Methoxy-benzenesulfonyl)-2,3-dihydro-1H-indol-7-yl]-benzenesulfonamide (compound 29),
N-[1-(4-Methoxy-benzenesulfonyl)-2,3-dihydro-1H-indol-7-yl]-4-nitro-benzenesulfonamide (compound 30),
4-Fluoro-N-[1-(4-methoxy-benzenesulfonyl)-2,3-dihydro-1H-indol-7-yl]-benzenesulfonamide (compound 31),
[1-(4-Methoxy-benzenesulfonyl)-2,3-dihydro-1H-indol-7-yl]-carbamic acid phenyl ester (compound 32),
3-[1-(4-Methoxy-benzenesulfonyl)-2,3-dihydro-1H-indol-7-yl]-1-methyl-1-phenyl-urea (compound 33),
Benzyl-[1-(4-methoxy-benzenesulfonyl)-2,3-dihydro-1H-indol-7-yl]-amine (compound 34),
N-[1-(4-Methoxy-benzenesulfonyl)-2,3-dihydro-1H-indol-7-yl]acetamide (compound 35),
N-[1-(4-Methoxy-benzenesulfonyl)-2,3-dihydro-1H-indol-7-yl]-2,2-dimethyl-propionamide (compound 36), N-[5-Bromo-1-(4-methoxy-benzenesulfonyl)-2,3-dihydro-1H-indol-7-yl]-isonicotinamide (compound 37),
Furan-2-carboxylic acid [5-bromo-1-(4-methoxy-benzenesulfonyl)-2,3-dihydro-1H-indol-7. -yl]-amide (compound 38), and
N-[1-(4-Methoxy-benzenesulfonyl)-2,3-dihydro-1H-indol-7-yl]-N-oxide-isonicotinamide (compound 39).

The application field of the indoline-sulfonamide compounds of the present invention is not limited. Preferably, the indoline-sulfonamide compounds of the present invention are used for inhibiting tubulin polymerization, and tubulin polymerization related cancers or angiogenesis related diseases.

In addition, the present invention further provides a pharmaceutical composition, comprising the indoline-sulfonamide compound of the present invention and a pharmaceutically acceptable carrier to inhibit tubulin polymerization, or tubulin polymerization related cancers or diseases.

The indoline-sulfonamide compounds of the present invention encompass the compounds themselves, their pharmaceutically acceptable salts, and prodrugs thereof. For example, the salt can be prepared by reacting the positive group (such as amino) of the compound with an anion. The satiable anions include, but are not limited to chloride, bromide, iodide, sulfate, nitrate, phosphate, citrate, alkylsulfonate, trifluoroacetate, and acetate. Also, the salt can be prepared by reacting the negative group (such as carboxy) with a cation. The satiable cations include, but are not limited to sodium, potassium, magnesium, calcium, and ammonium (such as tetramethylammonium). The examples of the prodrugs include the ester derivatives derived from the aforementioned compounds and other pharmaceutically acceptable derivatives.

A non-aromatic double bond and one or more asymmetric centers may exist in the indoline-sulfonamide compounds of the present invention. The chemical structure depicted herein encompasses meso compounds, racemic mixtures, enantiomers, diastereomers, diastereomer mixtures, cis-isomers, and trans-isomers. The present invention encompasses all isomeric forms, including E-form isomers, and Z-form isomers.

The pharmaceutical composition comprising the indoline-sulfonamide compounds of the present invention can be administered intravenously, orally, nasally, rectally, locally, or sublingually. Intravenous administration includes subcutaneous, intraperitoneal, intravenous, intramuscular, intraarticular, intraaortic, intrapleural, spinal, intrathecal, local injection at the site attacked by a disease, or other suitable administration techniques.

The sterile injectable composition can be a solution, or suspension in a non-toxic intravenous diluent or solvent (such as 1,3-butanediol). The acceptable carrier or solvent can be mannitol or water. In addition, the fixed oil is conventionally employed as a solvent or suspending medium (such as synthetic mono- or diglycerides). The fatty acid such as oleic acid and the glycerine ester derivative thereof can be used in the preparation of pharmaceutically acceptable injectables, such as olive oil or castor oil, especially in polyoxyethylated form. The oily solution or suspension can comprise long chain aliphatic alcohol diluents or dispersion, carboxymethylcellulose, or a similar dispersion. Examples of the generally used materials include surfactants (e.g. Tween, or Spans), other similar emulsifying agents, pharmaceutically acceptable solid, liquid generally used in the pharmaceutical industry, or other bioavailable potentiating agents used for developing new formulations.

The pharmaceutical composition may be in a form suitable for oral use, for example, as capsule, troche, emulsifying agent, liquid suspension, dispersion, or solvent. For administration in a troche form, the generally used carrier is lactose or corn starch, flotation reagent (e.g. magnesium stearate as an elementary additive). For oral administration in a capsule form, the useful diluents include lactose and corn starch. For oral administration in a liquid suspension or emulsifying agent, the active material can be suspended or dissolved in an oily medium containing an emulsifying agent or suspension. If necessary, suitable sweeteningagents, flavoring agents, or coloring agents can be added.

Compositions intended for nasal aerosol or inhalation may be prepared according to any method known to the art for the manufacture of pharmaceutical compositions. For example, the composition prepared in the isotonic sodium chloride solution can further contain benzyl alcohol or other suitable preservative, an absorbefacient to enhance bioavailability, fluorocarbon, or other known soluble dispersion. The compositions comprising one or more active compounds of the present invention may also be administered in the form of suppositories for rectal administration of the drug.

The carrier of the pharmaceutical composition containing indoline-sulfonamide compounds must be acceptable. The term "acceptable" means the carrier is compatible with the active ingredient (more preferably, the carrier can stabilize the active ingredient), and is not harmful to the patient. One or more agents can be a pharmaceutical elixir which can deliver the active compound of the present invention. Examples of other carriers include silicon oxide, magnesium stearate, cellulose, sodium lauryl sulfate, and D&C Yellow 10.

BRIEF DESCRIPTION OF THE DRAWINGS none

DETAILED DESCRIPTION OF THE PREFERRED EMBODIMENT

The indoline-sulfonamide compounds of the present invention, the analysis method thereof, and the determination method thereof are presented in the following:

Melting points were determined on a Büchi (B-545) melting point apparatus and are uncorrected.

Nuclear magnetic resonance ($^1$H NMR and $^{13}$C NMR) spectra were obtained with the Bruker DRX-500 spectrometer (operating at 500 MHz and at 125 MHz, respectively), Varian Mercury-400 spectrometer (operating at 400 MHz and at 100 MHz, respectively), and the Varian Mercury-300 spectrometer (operating at 300 MHz and at 75 MHz, respectively), with chemical shift in parts per million (ppm,δ) downfield from TMS as an internal standard.

High-resolution mass spectra (HRMS) were measured with a Finnigan (MAT-95XL) electron impact (EI) mass spectrometer.

Elemental analyses were performed on a Heraeus CHN—O Rapid microanalyzer.

Flash column chromatography was done using silica gel (Merck Kieselgel 60, No. 9385, 230-400 mesh ASTM).

All reactions were carried out under an atmosphere of dry nitrogen.

The general method for the synthesis of indoline-sulfonamides 19-38 is shown in Scheme 1.

Scheme 1

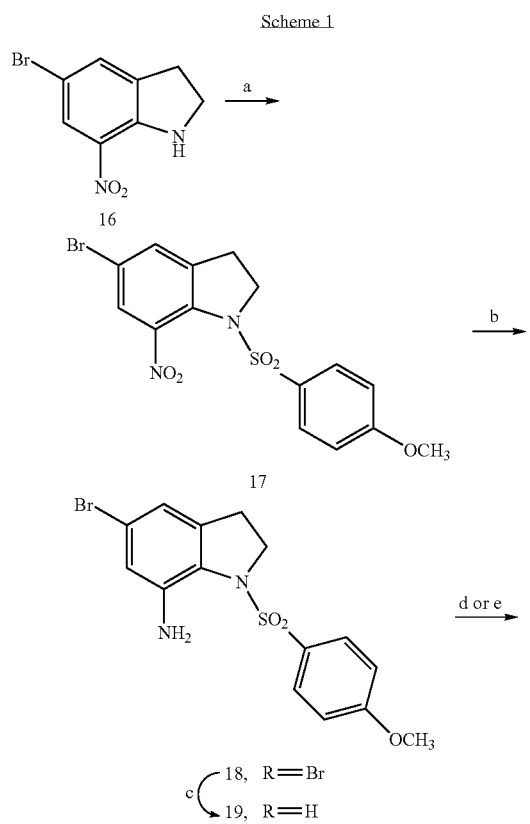

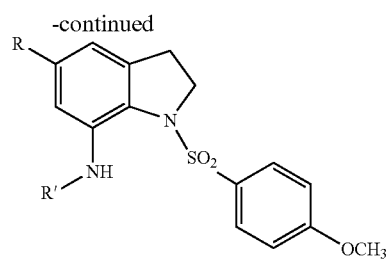

20-38 (37 and 38 are synthesized from 18)

The preparation involved a straightforward reaction sequence with high yields (overall 48-56% in three or four steps). The commercially available 5-bromo-7-nitroindoline (16) was reacted with the 4-methoxybenzenesulfonyl chloride in pyridine to afford the 5-bromo-1-(4-methoxybenzenesulfonyl)-7-nitroindoline (17).

The reduction of 7-nitro group in 17 with Fe/NH$_4$Cl in isopropanol gave the corresponding 18, namely 7-amino-5-bromo-1-(4-methoxybenzenesulfonyl)indoline.

Compound 18 was converted to the 7-amino-1-(4-methoxybenzene-sulfonyl)indoline (19) by a free radical-mediated debromination in the presence of AIBN and Bu$_3$SnH (as the pathway d in Scheme 1).

Compound 18 or 19 was further reacted with the corresponding electrophiles in pyridine (as the pathway d in Scheme 1), including aroyl chloride, heteroaroyl chloride, ArSO$_2$Cl, ArO(CO)Cl, ArN(CH$_3$)(CO)Cl, benzyl chloride, acetyl anhydride and pivaloyl chloride, to afford the desired 7-aminoindoline-1-sulfonamides (20-25, 27-36 and 38, respectively).

7-Isonicotinoyl substituted indolines, compound 26 and 37, were obtained respectively by treatment of 19 and 18 with isonicotinoyl chloride hydrochloride in the presence of Cs$_2$CO$_3$ in anhydrous CH$_3$CN (as the pathway e in Scheme 1).

The synthesis of compounds 17-39 and the chemical properties thereof are shown in the following examples.

EXAMPLE 1

5-Bromo-1-(4-methoxy-benzenesulfonyl)-7-nitro-2,3-dihydro-1H-indole (17)

A solution of 5-bromo-7-nitroindoline (5 g, 0.021 mol), 4-methoxyphenylsulfonyl chloride (6.36 g, 0.030 mol) in pyridine (10 ml) was stirred at 120° C. for 16 h. The reaction was quenched with water and extracted with CH$_2$Cl$_2$. The combined organic layer was dried over anhydrous MgSO$_4$ and evaporated to give a residue that was chromatographed over silica gel (EtOAc:n-hexane=1:2) to afford compound 17, yield 85%.

$^1$H NMR (300 MHz, CDCl$_3$) δ 2.67 (t, J=7.8 Hz, 2H), 3.87 (s, 3H), 4.05 (t, J=7.5 Hz, 2H), 6.92-6.97 (m, 1H), 7.50 (d, J=1.5 Hz, 1H), 7.62-7.66 (m, 2H), 7.89 (d, J=1.5 Hz, 1H).

$^{13}$C NMR (CDCl$_3$) δ 29.0, 51.8, 55.7, 114.4, 118.7, 126.4, 128.6, 129.4, 132.0, 134.7, 141.7, 142.5, 163.8.

MS (ESI) m/z: 436 (M+23)$^+$.

EXAMPLE 2

5-Bromo-1-(4-methoxy-benzenesulfonyl)-2,3-dihydro-1H-indol-7-yl amine (18)

A mixture of 17 (9 g, 0.021 mol), iron (3.65 g, 0.065 mol), and ammonium chloride (2.33 g, 0.043 mol) in isopropanol (200 ml)-water (50 ml) was stirred at 100° C. for 4 h. After cooling, the reaction mixture was filtrated and extracted with $CH_2Cl_2$. The combined organic layer was dried by $MgSO_4$ and evaporated to give a residue that was purified by silica gel flash column chromatography (EtOAc:n-hexane=2:3) to afford compound 18, yield 89%.

$^1$H NMR (400 MHz, $CDCl_3$) δ 2.13 (t, J=7.6 Hz, 2H), 3.84 (s, 3H), 3.95 (t, J=7.6 Hz, 2H), 4.80 (s, 2H), 6.53 (d, J=2.0 Hz, 1H), 6.74 (d, J=2.0 Hz, 1H), 6.85-6.89(m, 2H), 7.54-7.57 (m, 2H).

$^{13}$C NMR ($CDCl_3$) δ 28.9, 53.2, 55.5, 114.1, 117.0, 118.1, 120.4, 127.1, 128.0, 129.6, 140.4, 141.5, 163.5.

MS (ESI) m/z: 384 (M+1)$^+$, 385(M+2)$^+$.

EXAMPLE 3

1-(4-Methoxy-benzenesulfonyl)-2,3-dihydro-1H-indol-7-ylamine (19)

Compound 19

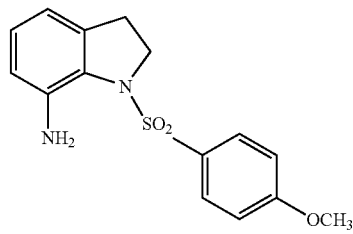

To a stirred solution of 18 (2 g, 4.84 mmol), AIBN (0.08 g, 0.48 mmol), $Bu_3SnH$ (3.91 ml, 14.50 mmol) in toluene (49 ml) was heated to reflux for 15 h. After cooling, the reaction mixture was evaporated and then extracted by $CH_2Cl_2$. The combined organic layer was dried by $MgSO_4$ and concentrated to give a residue that was purified by silica gel flash column chromatography (EtOAc:n-hexane=1:2) to give compound 19, yield 90%.

$^1$H NMR (500 MHz, $CDCl_3$) δ 2.15 (t, J=7.4 Hz, 2H), 3.82 (s, 3H), 3.95 (t, J=7.4 Hz, 2H), 6.42 (d, J=7.4 Hz, 1H), 6.59 (d, J=7.9 Hz, 1H), 6.81-6.84 (m, 2H), 6.90 (t, J=7.6 Hz, 1H), 7.51-7.54 (m, 2H).

MS (EI) m/z: 304 (M$^+$, 6%), 133 (100%). HRMS (EI) for $C_{15}H_{16}N_2O_3S$ (M$^+$): calcd, 304.0881; found, 304.0880.

EXAMPLE 4

N-[1-(4-Methoxy-benzenesulfonyl)-2,3-dihydro-1H-indol-7-yl]-benzamide (20)

Compound 20

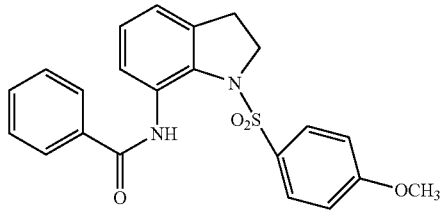

To a solution of 19(0.1 g, 0.26 mmol), benzoyl chloride (0.09 ml, 0.78 mmol) in pyridine (1 ml) was stirred at 100-110° C. for 16H. The reaction mixture was quenched with ice water and extracted with EtOAc. The combined organic layer was dried over anhydrous $MgSO_4$ and evaporated to give residue that was chromatographed over silica gel (EtOAc:n-hexane=1:2) to afford 20, yield 82%.

mp 205-206° C.

$^1$H NMR (400 mHz, $CDCl_3$) δ 2.25(t, J=7.6 Hz, 2H), 3.84(s, 3H), 4.03(t, J=7.6 Hz, 2H), 6.83-6.87(m, 3H), 7.20(t, J=7.6 Hz, 1H), 7.48-7.57(m, 5H), 8.06-8.09(m, 2H), 8.27(d, J=8.0 Hz, 1H), 10.23(s, 1H).

$^{13}$C NMR ($CDCl_3$) δ 29.0, 53.4, 55.6, 114.2, 120.5, 121.9, 127.4, 127.6, 128.6, 129.7, 130.5, 131.7, 131.8, 132.2, 134.6, 138.2, 163.8, 165.6.

MS (EI) m/z: 408(M$^+$, 7%), 237(62%), 105(100%). HRMS (EI) for $C_{22}H_{20}N_2O_4S$ (M$^+$): calcd, 408.1136; found, 408.1140. Anal. ($C_{22}H_{20}N_2O_4S$) C, H, N, S.

EXAMPLE 5

4-Fluoro-N-[1-(4-methoxy-benzenesulfonyl)-2,3-dihydro-1H-indol-7-yl]-benzamide (21)

Compound 21

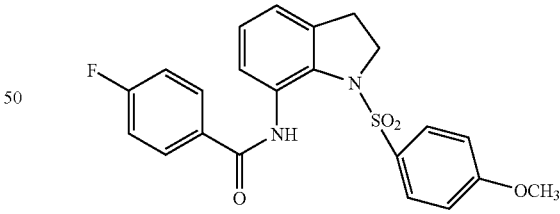

The title compound was obtained in 78% yield in a manner similar for the preparation of 20 by use of 4-fluorobenzoyl chloride.

mp 184-185° C.

$^1$H NMR (300 MHz, $CDCl_3$) δ 2.25 (t, J=7.5 Hz, 2H), 3.83 (s, 3H), 4.02 (t, J=7.5 Hz, 2H), 6.83-6.87 (m, 3H), 7.14-7.22 (m, 3H), 7.47-7.52 (m, 2H), 8.06-8.11 (m, 2H), 8.24 (d, J=8.1 Hz, 1H), 10.2 (s, 1H).

MS (EI) m/z: 426 (M$^+$, 11%), 255 (95%), 123 (100%). HRMS (EI) for $C_{22}H_{19}N_2O_4FS$ (M$^+$): calcd, 426.1046; found, 426.1048.

EXAMPLE 6

N-[1-(4-Methoxy-benzenesulfonyl)-2,3-dihydro-1H-indol-7-yl]-4-nitro-benzamide (22)

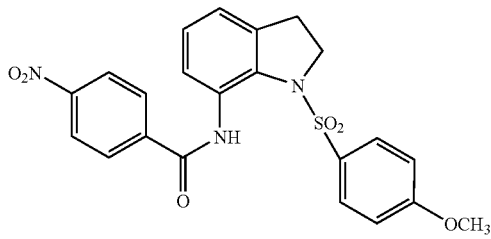

Compound 22

The title compound was obtained in 90% yield in a manner similar for the preparation of 20 by use of 4-nitrobenzoyl chloride. mp 151-152° C.

$^1$H NMR (300 MHz, CDCl$_3$) δ 2.28 (t, J=7.5 Hz, 2H), 3.84 (s, 3H), 4.04 (t, J=7.5 Hz, 2H), 6.84-6.91 (m, 3H), 7.23 (t, J=7.8 Hz, 1H), 7.48-7.53 (m, 2H), 8.21-8.26 (m, 3H), 8.34-8.38 (m, 2H), 10.4 (s, 1H).

$^{13}$C NMR (CDCl$_3$) δ 29.0, 53.5, 55.6, 114.3, 121.2, 121.8, 123.9, 127.4, 127.8, 128.6, 129.6, 130.9, 132.3, 138.4, 140.1, 149.8, 163.4, 163.9.

MS (EI) m/z: 453 (M$^+$, 100%), 282 (100%), 150 (65%). HRMS (EI) for C$_{22}$H$_{19}$N$_3$O$_6$S (M$^+$): calcd, 453.0993; found, 453.0994. Anal. (C$_{22}$H$_{19}$N$_3$O$_6$S) C, H, N, S.

EXAMPLE 7

4-Cyano-N-[1-(4-methoxy-benzenesulfonyl)-2,3-dihydro-1H-indol-7-yl]-benzamide (23)

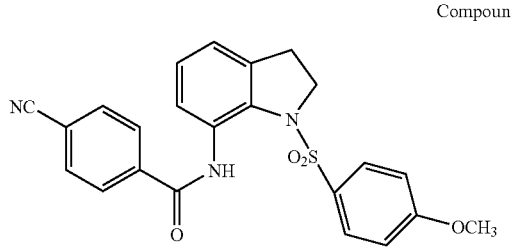

Compound 23

The title compound was obtained in 86% yield in a manner similar for the preparation of 20 by use of 4-cyanobenzoyl chloride.

mp 179-180° C.

$^1$H NMR (300 MHz, CDCl$_3$) δ 2.27 (t, J=7.2 Hz, 2H), 3.84 (s, 3H), 4.04 (t, J=7.5 Hz, 2H), 6.85-6.90 (m, 3H), 7.22 (t, J=8.1 Hz, 1H), 7.49-7.51 (m, 2H), 7.80-7.82 (m, 2H), 8.16-8.18 (m, 2H), 8.24 (d, J=8.1 Hz, 1H).

$^{13}$C NMR (CDCl$_3$) δ 29.2, 53.7, 55.9, 114.5, 115.7, 118.3, 121.3, 122.1, 127.6, 128.0, 128.3, 129.8, 131.2, 132.5, 132.8, 138.7, 138.8, 163.9, 164.2.

MS (EI) m/z: 433 (M$^+$, 12%), 262 (100%), 130 (73%). HRMS (EI) for C$_{23}$H$_{19}$N$_3$O$_4$S (M$^+$): calcd, 433.1098; found, 433.1097. Anal. (C$_{23}$H$_{19}$N$_3$O$_4$S) C, H, N, S.

EXAMPLE 8

4-Methoxy-N-[1-(4-methoxy-benzenesulfonyl)-2,3-dihydro-1H-indol-7-yl]-benzamide (24)

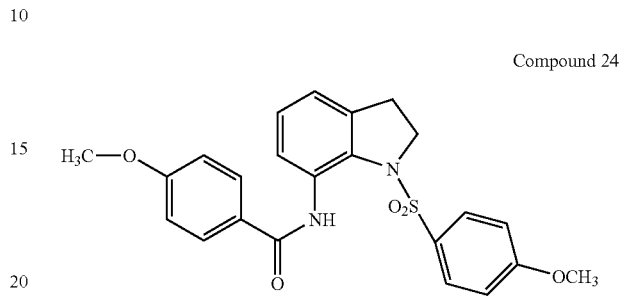

Compound 24

The title compound was obtained in 75% yield in a manner similar for the preparation of 20 by use of 4-methoxybenzoyl chloride.

$^1$H NMR (300 MHz, CDCl$_3$) δ 2.24 (t, J=7.5 Hz, 2H), 3.83 (s, 3H), 3.87 (s, 3H), 4.02 (t, J=7.8 Hz, 2H), 6.80-6.86 (m, 3H), 6.98-7.02 (m, 2H), 7.18 (t, J=8.1 Hz, 1H), 7.48-7.53 (m, 2H), 8.02-8.07 (m, 2H), 8.26 (d, J=8.1 Hz, 1H), 10.15 (s, 1H).

$^{13}$C NMR (CDCl$_3$) δ 29.0, 53.4, 55.2, 55.4, 113.7, 113.8, 114.2, 120.2, 121.8, 126.3, 126.8, 129.3, 129.6, 131.8, 131.9, 138.2, 162.4, 163.7, 165.1.

MS (EI) m/z: 438 (M$^+$, 4%), 267 (28%), 135 (100%). HRMS (EI) for C$_{23}$H$_{22}$N$_2$O$_5$S (M$^+$): calcd, 438.1237; found, 438.1243.

EXAMPLE 9

N-[1-(4-Methoxy-benzenesulfonyl)-2,3-dihydro-1H-indol-7-yl]-terephthalamic acid methyl ester (25)

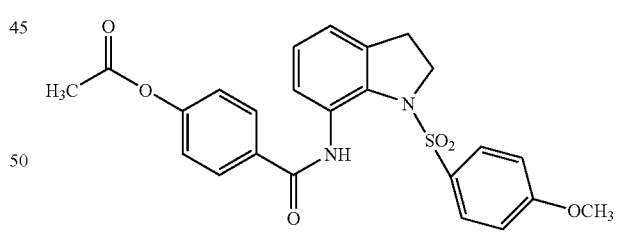

Compound 25

The title compound was obtained in 81% yield in a manner similar for the preparation of 20 by use of methyl 4-chlorocarbonylbenzoate. mp 166-167° C.

$^1$H NMR (300 MHz, CDCl$_3$) δ 2.25 (t, J=7.5 Hz, 2H), 3.82 (s, 3H), 3.94 (s, 3H), 4.02 (t, J=7.5 Hz, 2H), 6.82-6.87 (m, 3H), 7.20 (t, J=7.5 Hz, 1H), 7.47-7.52 (m, 2H), 8.11-8.18 (m, 4H), 8.26 (d, J=7.8 Hz, 1H).

$^{13}$C NMR (CDCl$_3$) δ 28.9, 52.2, 53.3, 55.5, 114.2, 120.8, 121.7, 127.3, 127.4, 127.6, 129.5, 129.8, 131.1, 132.1, 132.8, 138.3, 138.4, 163.7, 164.4, 166.2.

MS (EI) m/z: 466 (M$^+$, 14%), 295 (100%), 163 (89%). HRMS (EI) for C$_{24}$H$_{22}$N$_2$O$_6$S (M$^+$): calcd, 466.1194; found, 466.1196.

EXAMPLE 10

N-[1-(4-Methoxy-benzenesulfonyl)-2,3-dihydro-1H-indol-7-yl]-isonicotin amide (26)

Compound 26

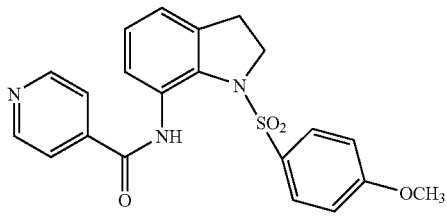

To a stirred mixture of 19 (0.2 g, 0.52 mmol), isonicotinoyl chloride hydrochloride (0.18 g, 1.04 mmol), and cesium carbonate (0.68 g, 2.08 mmol) in acetonitrile (20 ml) was heated to reflux for 16 h. The reaction mixture was quenched with ice water and extracted with $CH_2Cl_2$. The combined organic layer was dried over $MgSO_4$ and evaporated to give a residue that was purified by silica gel flash column chromatography (EtOAc:n-hexane :$NH_3$(aq)=3:2:1%) and recrystallized ($CH_2Cl_2$/EtOAc) to afford compound 26, yield 82%.

mp 219-220° C. (HCl salt).

$^1$H NMR (500 MHz, $CDCl_3$) δ 2.23 (t, J=7.3 Hz, 2H), 3.79 (s, 3H), 3.99 (t, J=7.4 Hz, 2H), 6.81-6.85 (m, 3H), 7.17 (t, J=7.8 Hz, 1H), 7.46 (d, J=8.8 Hz, 2H), 7.87 (d, J=5.7 Hz, 2H), 8.21 (d, J=8.2 Hz, 1H), 8.77 (d, J=5.6 Hz, 2H), 10.35 (s, 1H).

$^{13}$C NMR ($CDCl_3$) δ 28.8, 53.3, 55.5, 114.2, 120.9, 121.1, 121.7, 127.2, 127.6, 129.4, 130.7, 132.1, 138.3, 141.5, 150.6, 163.3, 163.8.

MS (EI) m/z: 409 (M$^+$, 36%), 314 (15%), 238 (100%). HRMS (EI) for $C_{21}H_{19}N_3O_4S$ (M$^+$): calcd, 409.1094; found, 409.1095. Anal. ($C_{21}H_{19}N_3O_4S$) C, H, N, S.

EXAMPLE 11

Furan-2-carboxylic acid [1-(4-methoxy-benzenesulfonyl)-2,3-dihydro -1H-indol-7-yl]-amide (27)

Compound 27

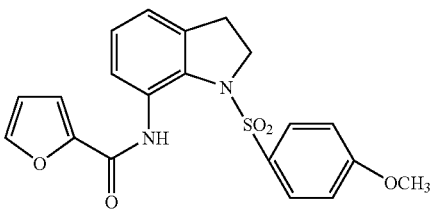

The title compound was obtained in 86% yield in a manner similar for the preparation of 20 by use of 2-furoyl chloride.

mp 163-164° C.

$^1$H NMR (400 MHz, $CDCl_3$) δ 2.24 (t, J=7.6 Hz, 2H), 3.83 (s, 3H), 4.03 (t, J=7.2 Hz, 2H), 6.53-6.55 (m, 1H), 6.83-6.87 (m, 3H), 7.18 (t, J=7.6 Hz, 1H), 7.25-7.26 (m, 1H), 7.48-7.52 (m, 2H), 7.60 (m, 1H), 8.22 (d, J=8.4 Hz, 1H), 10.25 (s, 1H).

$^{13}$C NMR ($CDCl_3$) δ 29.0, 53.3, 55.6, 112.0, 114.2, 115.0, 120.5, 121.7, 127.6, 127.7, 129.7, 131.0, 132.1, 138.3, 144.9, 148.0, 156.6, 163.7.

MS (EI) m/z: 398 (M$^+$, 13%), 303 (10%), 227 (100%). HRMS (EI) for $C_{20}H_{18}N_2O_5S$ (M$^+$): calcd, 398.0933; found, 398.0935. Anal. ($C_{20}H_{18}N_2O_5S$) C, H, N, S.

EXAMPLE 12

Thiophene-2-carboxylic acid [1-(4-methoxy-benzenesulfonyl)-2,3-dihydro -1H-indol-7-yl]-amide (28)

Compound 28

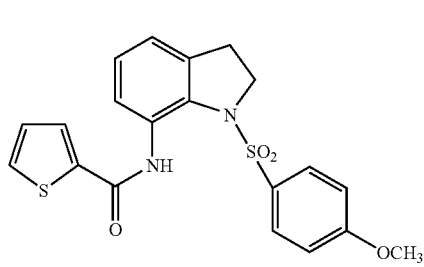

The title compound was obtained in 78% yield in a manner similar for the preparation of 20 by use of 2-thenoyl chloride.

mp 188-189° C.

$^1$H NMR (400 MHz, $CDCl_3$) δ 2.26 (t, J=7.6 Hz, 2H), 3.83 (s, 3H), 4.03 (t, J=7.6 Hz, 2H), 6.82-6.87 (m, 3H), 7.12-7.15 (m, 1H), 7.17 (t, J=7.6 Hz, 1H), 7.49-7.53 (m, 2H), 7.55 (dd, J=5.2 Hz, 1.2 Hz, 1H), 7.82 (dd, J=4.0, 1.2 Hz, 1H), 8.22 (d, J=8.0 Hz, 1H), 10.23 (s, 1H).

$^{13}$C NMR ($CDCl_3$) δ 29.0, 53.5, 55.6, 114.2, 120.4, 121.5, 127.5, 127.6, 127.9, 128.5, 129.6, 130.9, 131.2, 131.8, 138.2, 140.0, 160.1, 163.8.

MS (EI) m/z: 414 (M$^+$, 13%), 243 (100%), 111 (73%). HRMS (EI) for $C_{20}H_{18}N_2O_4S_2$ (M$^+$): calcd, 414.0704; found, 414.0706. Anal. ($C_{20}H_{18}N_2O_4S_2$) C, H, N, S.

EXAMPLE 13

N-[1-(4-Methoxy-benzenesulfonyl)-2,3-dihydro-1H-indol-7-yl]-benzenesulfonamide (29)

Compound 29

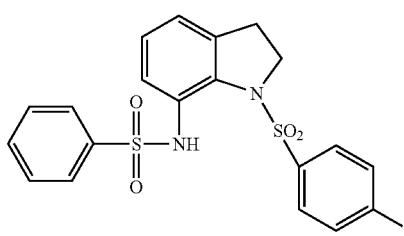

The title compound was obtained in 80% yield in a manner similar for the preparation of 20 by use of benzenesulfonyl chloride. mp 143-145° C.

$^1$H NMR (300 MHz, $CDCl_3$) δ 2.09 (t, J=7.2 Hz, 2H), 3.53 (t, J=7.5 Hz, 2H), 3.80 (s, 3H), 6.77 (d, J=8.7 Hz, 2H), 6.84 (d, J=7.2 Hz, 1H), 7.11 (t, J=7.5 Hz, 1H), 7.27-7.32 (m, 2H), 7.40 (m, 2H), 7.49-7.54 (m, 2H), 7.75 (d, J=7.8 Hz, 1H).

$^{13}$C NMR ($CDCl_3$) δ 28.7, 52.7, 55.6, 114.2, 122.3, 124.2, 127.3, 127.7, 128.5, 129.3, 129.4, 129.6, 132.5, 134.9, 138.3, 139.5, 163.7.

MS (EI) m/z: 444 (M+, 10%), 273 (85%), 132 (100%).
HRMS (EI) for $C_{21}H_{20}N_2O_5S_2$ (M+): calcd, 444.0812; found, 444.0813.

EXAMPLE 14

N-[1-(4-Methoxy-benzenesulfonyl)-2,3-dihydro-1H-indol-7-yl]-4-nitro-benzenesulfonamide (30)

Compound 30

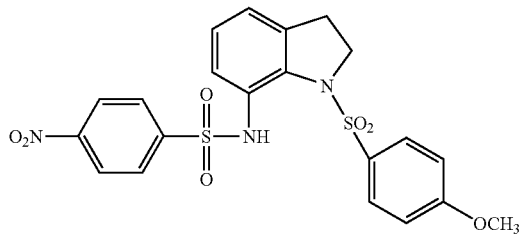

The title compound was obtained in 82% yield in a manner similar for the preparation of 20 by use of 4-nitrobenzenesulfonyl chloride.

$^1$H NMR (400 MHz, CDCl$_3$) δ 2.12 (t, J=7.2 Hz, 2H), 3.53 (t, J=7.2 Hz, 2H), 3.82 (s, 3H), 6.79-6.83 (m, 2H), 6.92 (dd, J=7.6, 1.2 Hz, 1H), 7.16 (t, J=7.6 Hz, 1H), 7.30-7.34 (m, 2H), 7.52 (d, J=8.0 Hz, 1H), 7.94-7.97 (m, 2H), 8.24-8.28 (m, 2H), 9.16 (s, 1H).

$^{13}$C NMR (CDCl$_3$) δ 28.7, 52.8, 55.6, 114.3, 123.2, 123.7, 124.8, 127.0, 128.0, 128.4, 128.7, 129.4, 135.2, 138.5, 145.5, 149.9, 163.9.

MS (EI) m/z: 489 (M+, 13%), 318 (100%), 132 (72%). HRMS (EI) for $C_{21}H_{19}N_3O_7S_2$ (M+): calcd, 489.0654; found, 489.0659.

EXAMPLE 15

4-Fluoro-N-[1-(4-methoxy-benzenesulfonyl)-2,3-dihydro-1H-indol-7-yl]-benzenesulfonamide (31)

Compound 31

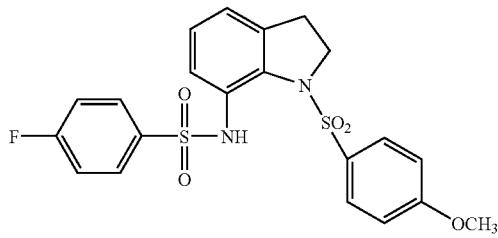

The title compound was obtained in 83% yield in a manner similar for the preparation of 20 by use of 4-fluorobenzenesulfonyl chloride. mp 104-105° C.

$^1$H NMR (300 MHz, CDCl$_3$) δ 2.11 (t, J=7.5 Hz, 2H), 3.58 (t, J=7.8 Hz, 2H), 3.81 (s, 3H), 6.77-6.81 (m, 2H), 6.86 (dd, J=7.8, 1.2 Hz, 1H), 7.05-7.15 (m, 3H), 7.30-7.34 (m, 2H), 7.50 (d, J=8.0 Hz, 1H), 7.75-7.80 (m, 2H), 8.97 (s, 1H).

MS (EI) m/z: 462 (M+, 13%), 291 (100%), 132 (59%). HRMS (EI) for $C_{21}H_{19}N_2O_5S_2F$ (M+): calcd, 462.0729; found, 462.0724.

EXAMPLE 16

[1-(4-Methoxy-benzenesulfonyl)-2,3-dihydro-1H-indol-7-yl]-carbamic acid phenyl ester (32)

Compound 32

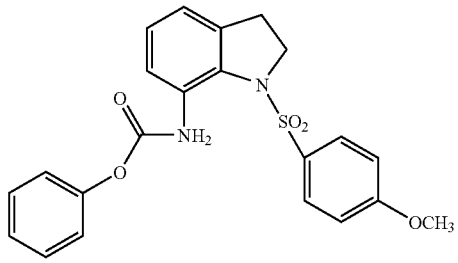

The title compound was obtained in 76% yield in a manner similar for the preparation of 20 by use of phenyl chloroformate.

mp 164-166° C.

$^1$H NMR (300 mHz, CDCl$_3$) δ 2.29(t, J=7.8 Hz, 2H), 3.75(s, 3H), 4.00(t, J=7.5 Hz, 2H), 6.75-6.80(m, 2H), 7.07 (dd, J=7.5, 0.6 Hz, 1H), 7.16-7.25(m, 4H), 7.30-7.40(m, 4H), 7.57-7.62(m, 2H).

$^{13}$C NMR (CDCl$_3$) δ 29.0, 53.1, 55.5, 114.0, 121.5, 121.6, 125.1, 125.9, 127.0, 129.1, 129.2, 129.3, 129.6, 130.6, 138.9, 139.1, 150.7, 163.3.

MS (ESI) m/z: 425(M+H)+.

EXAMPLE 17

3-[1-(4-Methoxy-benzenesulfonyl)-2,3-dihydro-1H-indol-7-yl]-1-methyl-1-phenyl-urea (33)

Compound 33

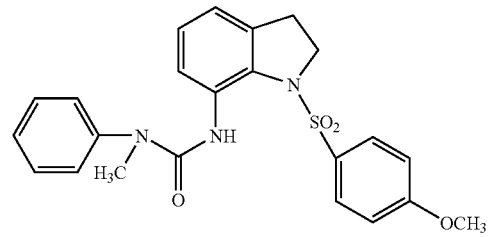

The title compound was obtained in 75% yield in a manner similar for the preparation of 20 by use of N-methyl-N-phenylcarbamoyl chloride. mp 199-201° C.

$^1$H NMR (400 MHz, CDCl$_3$) δ 2.07 (t, J=7.2 Hz, 2H), 3.38 (s, 3H), 3.80 (s, 3H), 3.83 (t, J=7.2 Hz, 2H), 6.71 (d, J=8.0 Hz, 1H), 6.75-6.78 (m, 2H), 7.12 (t, J=7.8 Hz, 1H), 7.29-7.33 (m, 2H), 7.35-7.39 (m, 1H), 7.40-7.43 (m, 2H), 7.48-7.52 (m, 2H), 7.93 (d, J=8.0 Hz, 1H), 8.28 (s, 1H).

$^{13}$C NMR (CDCl$_3$) δ 28.8, 37.4, 53.0, 55.5, 113.9, 119.0, 122.0, 127.3, 127.6, 127.7, 127.8, 129.6, 130.0, 132.2, 132.9, 137.8, 142.6, 155.1, 163.5.

MS (EI) m/z: 437 (M+, 9%), 266 (100%), 159 (81%). HRMS (EI) for $C_{23}H_{23}N_3O_4S$ (M+): calcd, 437.1405; found, 437.1408.

EXAMPLE 18

Benzyl-[1-(4-methoxy-benzenesulfonyl)-2,3-dihydro-1H-indol-7-yl]-amine (34)

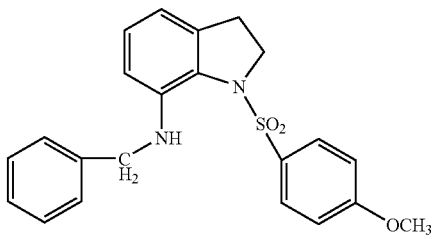

Compound 34

The title compound was obtained in 85% yield in a manner similar for the preparation of 20 by use of benzyl chloride. mp 162-163° C.

$^1$H NMR (300 MHz, CDCl$_3$) δ 1.98 (t, J=7.2 Hz, 2H), 3.75 (t, J=7.2 Hz, 2H), 3.77 (s, 3H), 4.72 (s, 3H), 6.42 (d, J=7.2 Hz, 1H), 6.70-6.76 (m, 2H), 6.92 (t, J=7.5 Hz, 1H), 7.14-7.27 (m, 4H), 7.35-7.40 (m, 4H).

$^{13}$C NMR (CDCl$_3$) δ 28.7, 51.9, 55.3, 55.4, 113.7, 115.2, 118.4, 126.5, 127.7, 128.1, 128.9, 129.8, 130.4, 139.3, 139.4, 143.7, 163.2.

MS (ESI) m/z: 395 (M+H)$^+$.

EXAMPLE 19

N-[1-(4-Methoxy-benzenesulfonyl)-2,3-dihydro-1H-indol-7-yl]acetamide (35)

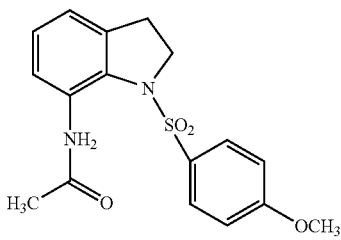

Compound 35

The title compound was obtained in 89% yield in a manner similar for the preparation of 20 by use of acetic anhydride. mp 154-155° C.

$^1$H NMR (300 mHz, CDCl$_3$) δ 2.20(t, J=7.5 Hz, 2H), 2.23(s, 3H), 3.83(s, 3H), 4.00(t, J=7.5 Hz, 2H), 6.79(d, J=7.8 Hz, 1H), 6.82-6.86(m, 2H), 7.13(t, J=7.9 Hz, 1H), 7.44-7.48 (m, 2H), 8.10(d, J=8.4 Hz, 1H), 8.35(s, 1H).

$^{13}$C NMR (CDCl$_3$) δ 24.7, 28.9, 53.4, 55.6, 114.2, 120.2, 121.5, 127.5, 127.6, 129.5, 131.4, 131.5, 138.0, 163.7, 168.8.

MS (EI) m/z: 346(M$^r$, 18%), 175(44%), 133(100%). HRMS (EI) for C$_{17}$H$_{18}$N$_2$O$_4$S (M$^r$): calcd, 346.0979; found, 346.0983. Anal. (C$_{17}$H$_{18}$N$_2$O$_4$S) C, H, N, S.

EXAMPLE 20

N-[1-(4-Methoxy-benzenesulfonyl)-2,3-dihydro-1H-indol-7-yl]-2,2-dimethyl-propionamide (36)

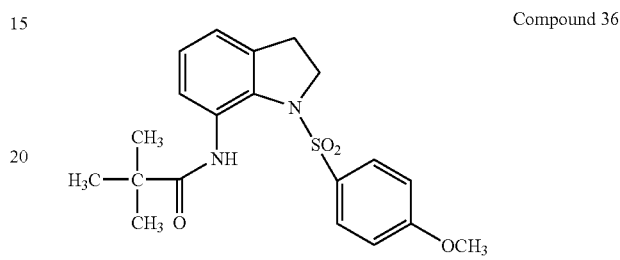

Compound 36

The title compound was obtained in 87% yield in a manner similar for the preparation of 20 by use of pivaloyl chloride.

$^1$H NMR (300 MHz, CDCl$_3$) δ 1.37 (s, 9H), 2.19 (t, J=7.2 Hz, 2H), 3.83 (s, 3H), 3.98 (t, J=7.5 Hz, 2H), 6.79 (d, J=7.5 Hz, 1H), 6.82-6.85 (m, 2H), 7.13 (t, J=7.8 Hz, 1H), 7.45-7.48 (m, 2H), 8.09 (d, J=8.1 Hz, 1H), 9.53 (s, 1H).

$^{13}$C NMR (CDCl$_3$) δ 27.6, 28.5, 39.9, 53.3, 55.6, 114.1, 120.1, 122.0, 127.5, 127.7, 129.7, 131.8, 132.1, 138.1, 163.7, 177.6.

MS (EI) m/z: 388 (M$^+$, 13%), 217 (51%), 167 (100%). HRMS (EI) for C$_{20}$H$_{24}$N$_2$O$_4$S (M$^+$): calcd, 388.1449; found, 388.1453.

EXAMPLE 21

N-[5-Bromo-1-(4-methoxy-benzenesulfonyl)-2,3-dihydro-1H-indol-7-yl]-isonicotinamide (37)

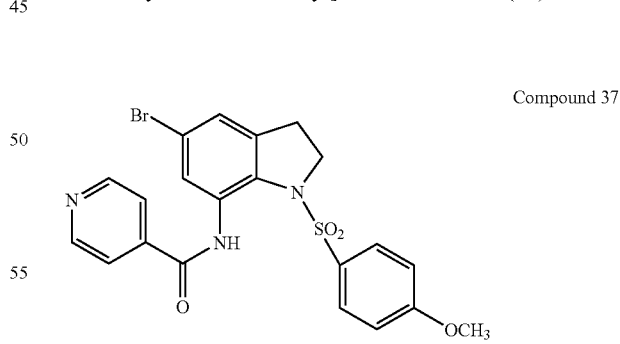

Compound 37

The title compound was obtained in 80% yield in a manner similar for the preparation of 26 starting from compound 18. mp 191-192° C.

$^1$H NMR (300 MHz, CDCl$_3$) δ 2.27 (t, J=7.2 Hz, 2H), 3.86 (s, 3H), 4.04 (t, J=7.5 Hz, 2H), 6.89-6.93 (m, 2H), 7.02 (d, J=1.8 Hz, 1H), 7.51-7.56 (m, 2H), 7.88-7.90 (m, 2H), 8.51 (d, J=1.8 Hz, 1H), 8.82-8.84 (m, 2H), 10.3 (s, 1H).

$^{13}$C NMR (CDCl$_3$) δ 28.8, 53.6, 55.6, 114.5, 120.6, 120.9, 124.1, 124.3, 127.0, 129.5, 131.2, 131.8, 140.1, 141.1, 150.7, 163.4, 164.0.

MS (EI) m/z: 490(M$^+$+2, 3%), 489(M$^+$+1, 12%), 488 (M$^+$, 3%), 487 (M$^+$−1, 11%), 318 (100%), 316 (98%). HRMS (EI) for C$_{21}$H$_{18}$N$_3$O$_4$SBr (M$^+$+1): calcd, 489.0178; found, 489.0180.

EXAMPLE 22

Furan-2-carboxylic acid [5-bromo-1-(4-methoxy-benzenesulfonyl)-2,3-dihydro-1H-indol-7-yl]-amide (38)

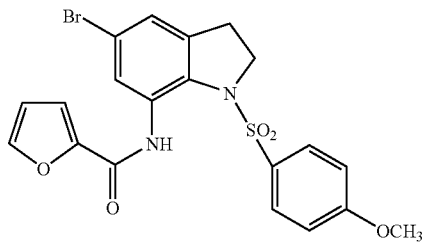

Compound 38

The title compound was obtained in 80% yield in a manner similar for the preparation of 20 starting from compound 18. mp 170-171° C.

$^1$H NMR (400 MHz, CDCl$_3$) δ 2.23 (t, J=7.6 Hz, 2H), 3.86 (s, 3H), 4.03 (t, J=7.6 Hz, 2H), 6.55 (m, 1H), 6.88-6.91 (m, 2H), 6.97 (d, J=1.6 Hz, 1H), 7.26-7.27 (m, 1H), 7.52-7.56 (m, 2H), 7.61 (m, 1H), 8.49 (d, J=1.6 Hz, 1H), 10.24 (s, 1H).

$^{13}$C NMR (CDCl$_3$) δ 28.9, 53.5, 55.6, 112.2, 114.4, 115.5, 120.5, 123.5, 124.2, 127.4, 129.7, 131.1, 132.1, 140.0, 145.1, 147.6, 156.5, 163.9.

MS (EI) m/z: 479(M$^+$+2, 3%), 478(M$^+$+1, 13%), 477 (M$^+$, 3%), 476 (M$^+$−1, 12%), 307 (99%), 305 (100%). HRMS (EI) for C$_{20}$H$_{17}$N$_2$O$_5$SBr (M$^+$+1): calcd, 478.0017; found, 478.0016.

EXAMPLE 23

N-[1-(4-Methoxy-benzenesulfonyl)-2,3-dihydro-1H-indol-7-yl]-N-oxide-isonicotinamide (39)

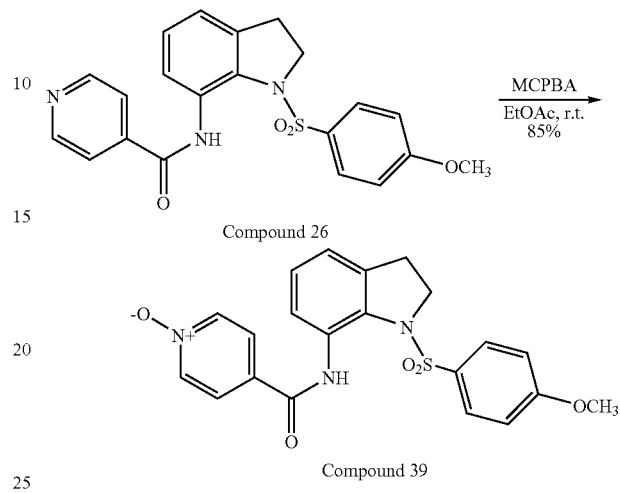

To a solution of compound 26 (0.27 g, 0.24 mmol) and m-chloroperbenzoic acid (0.3 g, 0.49 mmol) in EtOAc (10 ml) was stirred at room temperature for 5 h. The reaction mixture was quenched with NaHCO$_3$ and extracted by CH$_2$Cl$_2$ (x3). The combined organic layer was dried over anhydrous MgSO$_4$ and evaporated to give residue that was chromatographed over silica gel (CH$_2$Cl$_2$: MeOH=15:1) to afford the desired compound 39, yield 85%.

$^1$H NMR (300 MHz, CDCl$_3$) δ 2.29 (t, J=7.5 Hz, 2H), 3.84 (s, 3H), 4.05 (t, J=7.4 Hz, 2H), 6.84-6.91 (m, 3H), 7.22 (t, J=7.8 Hz, 1H), 7.50 (m, 2H), 7.97 (m, 2H), 8.21 (d, J=8.1 Hz, 1H), 8.29 (m, 2H), 10.38 (s, 1H).

$^{13}$C NMR (CDCl$_3$) δ 28.9, 53.5, 55.6, 114.3, 121.2, 121.6, 124.6, 127.2, 127.8, 129.5, 130.6, 130.9, 132.1, 138.4, 139.4, 161.2, 163.9.

MS (ESI) m/z: 426 (M+1)$^+$.

EXAMPLE 24

Elemental Analyses of Compounds 20, 22, 23, 26, 27, 28, and 35

| Compd | formula | calculated | | | | found | | | |
|---|---|---|---|---|---|---|---|---|---|
| | | % C | % H | % N | % S | % C | % H | % N | % S |
| 20 | C$_{22}$H$_{20}$N$_2$O$_4$S | 64.69 | 4.94 | 6.86 | 7.85 | 64.72 | 4.81 | 6.61 | 7.71 |
| 22 | C$_{22}$H$_{19}$N$_3$O$_6$S | 58.27 | 4.22 | 9.27 | 7.07 | 58.49 | 4.19 | 9.01 | 7.08 |
| 23 | C$_{23}$H$_{19}$N$_3$O$_4$S | 63.73 | 4.42 | 9.69 | 7.40 | 63.61 | 4.58 | 9.72 | 7.31 |
| 26 | C$_{21}$H$_{19}$N$_3$O$_4$S | 61.60 | 4.68 | 10.26 | 7.83 | 61.54 | 4.71 | 10.18 | 7.88 |
| 27 | C$_{20}$H$_{18}$N$_2$O$_5$S | 60.29 | 4.55 | 7.03 | 8.05 | 60.40 | 4.38 | 7.19 | 8.21 |
| 28 | C$_{20}$H$_{18}$N$_2$O$_4$S$_2$ | 57.95 | 4.38 | 6.76 | 15.47 | 58.01 | 4.25 | 6.78 | 15.29 |
| 35 | C$_{17}$H$_{18}$N$_2$O$_4$S | 58.94 | 5.24 | 8.09 | 9.26 | 58.86 | 5.28 | 7.88 | 9.14 |

EXAMPLE 25

Biological Test

Regents for cell culture were obtained from Gibco-BRL Life Technologies (Gaitherburg, Md.). Microtubule-associated protein (MAP)-rich tubulin was purchased from Cytoskeleton, Inc. (Denver, Colo.). [$^3$H]Colchicine (specific activity, 60-87 Ci/mmol) was purchased from PerkinElmer Life Sciences (Boston, Mass.).

(a) Cell Growth Inhibitory Assay

Human oral epidermoid carcinoma KB cells, colorectal carcinoma HT29 cells, non small cell lung carcinoma H460 cells, and two stomach carcinoma TSGH, MKN45 cells were maintained in RPMI-1640 medium supplied with 5% fetal bovine serum.

KB-VIN10 cells were maintained in growth medium supplemented with 10 nM vincristine, generated from vincristine-driven selection, and displayed overexpression of P-gp 170/MDR.

Cells in logarithmic phase were cultured at a density of 5000 cells/mL/well in a 24-well plate. KB-VIN10 cells were cultured in drug-free medium for 3 days prior to use. The cells were exposed to various concentrations of the test drugs for 72 h. The methylene blue dye assay was used to evaluate the effect of the test compounds on cell growth as described previously. The IC$_{50}$ value resulting from 50% inhibition of cell growth was calculated graphically as a comparison with the control.

The result of the examination shows that among the compounds 19-39 of the present invention, IC$_{50}$ of at least seventeen compounds is <5 μM, and IC$_{50}$ of the other compounds is <10 nM.

(b) Tubulin Polymerization in Vitro Assay

Turbidimetric assays of microtubules were performed as described by Bollag et al.

MAP-rich tubulin (2 mg/mL) in 100 mL buffer containing 100 mM PIPES (pH 6.9), 2 mM MgCl$_2$, 1 mM GTP, and 2% (v/v) dimethyl sulfoxide were placed in a 96-well microtiter plate in the presence of test compounds. The increase in absorbance was measured at 350 nm in a PowerWave X Microplate Reader (BIO-TEK Instruments, Winooski, Vt.) at 37° C. and recorded every 30 s for 30 min. The area under the curve (AUC) was used to determine the concentration that inhibited tubulin polymerization to 50% (IC$_{50}$). The AUC of the untreated control and 10 μM of colchicine was set to 100% and 0% polymerization, respectively, and the IC$_{50}$ was calculated by nonlinear regression in at least three experiments.

According to the results, the tested sulfonamide compounds (<2 μM, in the average) exhibit the property of inhibiting tubulin polymerization.

Although the present invention has been explained in relation to its preferred embodiment, it is to be understood that many other possible modifications and variations can be made without departing from the spirit and scope of the invention as hereinafter claimed.

What is claimed is:

1. An indoline-sulfonamide compound of the following formula (I):

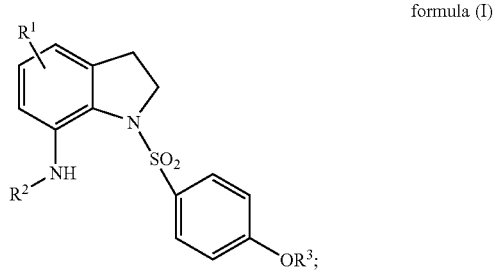

formula (I)

wherein R$^1$ is H, or halogen;

R$^2$ is H, Ar, Ar—C(O)—, Ar—CH$_2$—, Ar—SO$_2$—, Ar—O—C(O),

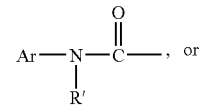

R"—C(O)—, and Ar is substituted or unsubstituted C5-C20 aryl, cyclyl,

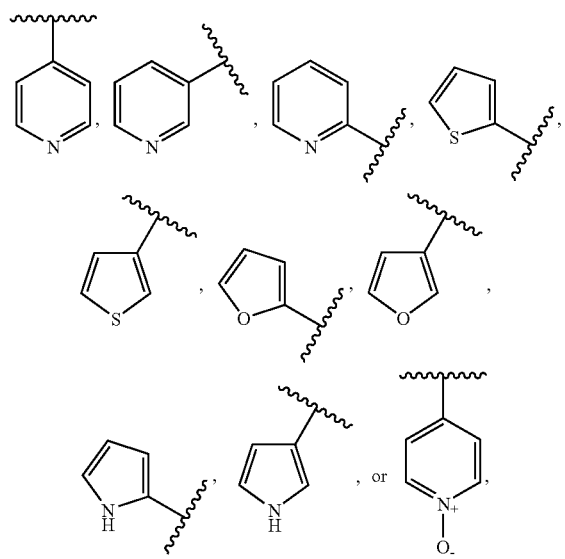

R' and R" independently, is C1-C10 alkyl, or C1-C10 alkoxyl; and

R$^3$ are C5-C15 aryl or C1-C10 alkyl.

2. The compound as claimed in claim 1, wherein R$^1$ is H or Br.

3. The compound as claimed in claim 1, wherein Ar is unsubstituted phenyl.

4. The compound as claimed in claim 1, wherein Ar is substituted or unsubstituted C5-C8 aryl.

5. The compound as claimed in claim 1, wherein Ar is aryl with a substituent, and the substituent is halogen, nitro, cyano, alkoxyl, acetoxyl (CH$_3$CO$_2^-$), or oxyl.

6. The compound as claimed in claim 1, wherein the halogen is F, Cl, or Br.

7. The compound as claimed in claim 1, wherein $R^2$ is benzoyl, fluorobenzoyl, nitrobenzoyl, cyanobenzoyl, methoxybenzoyl, or acetylbenzoyl.

8. The compound as claimed in claim 1, wherein $R^2$ is isonicotinoyl, N-oxide-isonicotinoyl, furoyl, or thienoyl.

9. The compound as claimed in claim 1, wherein $R^2$ is benzenesulfonyl, nitrobenzenesulfonyl, or fluorobenzenesulfonyl.

10. The compound as claimed in claim 1, wherein $R^2$ is $(CO)OC_6H_5$, or $(CO)N(CH_3)C_6H_5$.

11. The compound as claimed in claim 1, wherein $R^2$ is benzyl, acetyl, or pivaloyl.

12. The compound as claimed in claim 1, wherein $R^3$ is C1-C10 alkyl.

13. The compound as claimed in claim 12, wherein $R^3$ is methyl.

14. The compound as claimed in claim 1, wherein the compound is 1-(4-Methoxy-benzenesulfonyl)-2,3-dihydro-1H-indol-7-ylamine.

15. The compound as claimed in claim 1, wherein the compound is 1-(4-Methoxy-benzenesulfonyl)-2,3-dihydro-1H-indol-7-ylamine, 4-Fluoro-N-[1-(4-methoxy-benzenesulfonyl)-2,3-dihydro-1H-indol-7-yl]-benzamide, N-[1-(4-Methoxy-benzenesulfonyl)-2,3-dihydro-1H-indol-7-yl]-4-nitro-benzamide, 4-Cyano-N-[1-(4-methoxy-benzenesulfonyl)-2,3-dihydro-1H-indol-7-yl]-benzamide, 4-Methoxy-N-[1-(4-methoxy-benzenesulfonyl)-2,3-dihydro-1H-indol-7-yl]-benzamide, or N-[1-(4-Methoxy-benzenesulfonyl)-2,3-dihydro-1H-indol-7-yl]-terephthalamic acid methyl ester.

16. The compound as claimed in claim 1, wherein the compound is

N-[1-(4-Methoxy-benzenesulfonyl)-2,3-dihydro-1H-indol-7-yl]-isonicotinamide,

Furan-2-carboxylic acid [1-(4-methoxy-benzenesulfonyl)-2,3-dihydro-1H-indol-7-yl]-amide, or Thiophene-2-carboxylic acid [1-(4-methoxy-benzenesulfonyl)-2,3-dihydro-1H-indol-7-yl]-amide.

17. The compound as claimed in claim 1, wherein the compound is

N-[1-(4-Methoxy-benzenesulfonyl)-2,3-dihydro-1H-indol-7-yl]-benzenesulfonamide,

N-[1-(4-Methoxy-benzenesulfonyl)-2,3-dihydro-1H-indol-7-yl]4-nitro-benzenesulfon amide, or 4-Fluoro-N-[1-(4-methoxy-benzenesulfonyl)-2,3-dihydro-1H-indol-7-yl]-benzenesulfonamide.

18. The compound as claimed in claim 1, wherein the compound is [1-(4-Methoxy-benzenesulfonyl)-2,3-dihydro-1H-indol-7-yl]-carbamic acid phenyl ester, or 3-[1-(4-Methoxy-benzenesulfonyl)-2,3-dihydro-1H-indol-7-yl]-1-methyl-1-phenyl-urea.

19. The compound as claimed in claim 1, wherein the compound is

Benzyl-[1-(4-methoxy-benzenesulfonyl)-2,3-dihydro-1H-indol-7-yl]-amine,

N-[1-(4-Methoxy-benzenesulfonyl)-2,3-dihydro-1H-indol-7-yl]-acetamide, or

N-[1-(4-Methoxy-benzenesulfonyl)-2,3-dihydro-1H-indol-7-yl]-2,2-dimethyl-propionamide.

20. The compound as claimed in claim 1, wherein the compound is

N-[5-Bromo-1-(4-methoxy-benzenesulfonyl)-2,3-dihydro-1H-indol-7-yl]-isonicotinamide, Furan-2-carboxylic acid [5-bromo-1-(4-methoxy-benzenesulfonyl)-2,3-dihydro-1H-indol-7-yl]-amide, or N-[1-(4-Methoxy-benzenesulfonyl)-2,3-dihydro-1H-indol-7-yl]-N-oxide-isonicotinamide.

21. The compound as claimed in claim 1, wherein the compound is a cellular tubulin polymerization the term inhibitor.

22. The compound as claimed in claim 1, wherein the compound is a tubulin polymerization related cancer the term inhibitor.

23. The compound as claimed in claim 1, wherein the compound is combined with a pharmaceutically acceptable carrier to provide a pharmaceutical composition.

24. The compound as claimed in claim 1, wherein Ar is $C_5$-$C_8$ aryl, or $C_5$-$C_8$ cyclyl.

25. The compound of claim 1 wherein $R^1$ is H, $R^2$ is H and $R^3$ is methyl.

* * * * *